Sept. 17, 1974 F. W. ANDERSON Plant Pat. 3,620
DWARF PEACH TREE
Filed Sept. 7, 1973
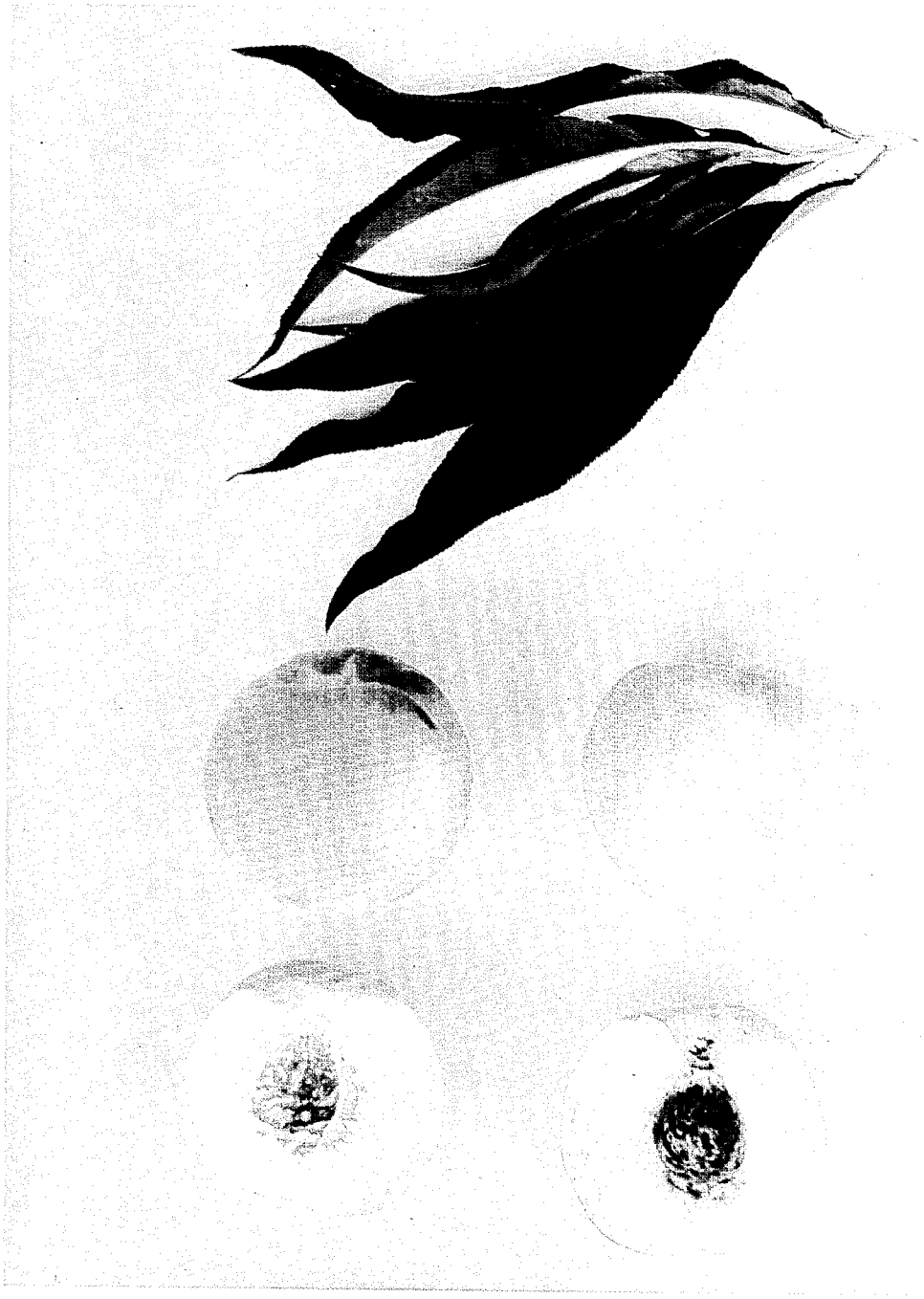

United States Patent Office

Plant Pat. 3,620
Patented Sept. 17, 1974

3,620

DWARF PEACH TREE

Frederic W. Anderson, Merced, Calif., assignor to
L. E. Cooke Co., Visalia, Calif.

Filed Sept. 7, 1973, Ser. No. 395,353
Int. Cl. A01h 5/03
U.S. Cl. Plt.—43 1 Claim

ABSTRACT OF THE DISCLOSURE

A genetically dwarf peach tree which is medium size, medium vigorous, spreading, foliated with large lanceolate leaves having a crenate margin and globose glands, and a productive bearer of uniform, large, symmetrical, globose, freestone fruit having yellow skin substantially overspread with red, and firm, crisp, melting, yellow flesh flecked with red.

*Background of the variety*: Over a substantial number of years I have engaged in an extensive and continuing plant breeding program at my experimental nursery and orchard located near Le Grand, Merced County, California; one purpose of such program being to provide improved varieties of fruit trees. The present variety of dwarf peach tree resulted from my endeavors in the conduit of such plant breeding program.

*Origin of the variety*: The present variety of dwarf peach tree was originated by me in my aforesaid experimental nursery and orchard as on $F_1$ cross between the Empress dwarf peach (U.S. Plant Pat. No. 2,533) as the seed parent, and the Bonanza dwarf peach (U.S. Plant Pat. No. 2,213) as the pollen parent.

*Asexual reproduction of the variety*: Upon recognition by me of the novel and distinctive characteristics of the present variety of dwarf peach tree, I asexually reproduced it by budding on mature orchard trees in my said experimental orchard. Such reproductions, in maturity, ran true to the original tree in all respects.

*Summary of the variety*: The present genetically dwarf peach tree is of medium size, medium vigorous, spreading, foliated with large lanceolate leaves having a crenate margin and globose glands, and a productive bearer of uniform, large, symmetrical, globose, freestone fruit having yellow skin substantially overspread with red, and firm, crisp, melting, yellow flesh flecked with red; the fruit of the variety being larger in size, firmer of flesh, and ripening at least one week earlier than the seed parent, Empress, and ripening about two weeks later than the pollen parent, Bonanza.

*Brief description of the drawing*: The drawing is an illustration, by photographic reproduction in color, of leaves of the variety, and separate fruit; one of the latter being cut in half to expose the flesh, with the stone remaining in one of the halves.

*Description of the variety*: The botanical details of this new and distinct variety of dwarf peach tree—with color definitions (except those in common color terms) referenced to Maerz and Paul Dictionary of Color—are as follows:

Tree:
- *Class.*—Genetically dwarf.
- *Size.*—Medium.
- *Vigor.*—Medium.
- *Growth.*—Spreading.
- *Production.*—Productive.

Trunk:
- *Size.*—Medium.
- *Texture.*—Medium.

Branches:
- *Size.*—Stocky.
- *Texture.*—Medium.
- *Color.*—Green.

Leaves:
- *Size.*—Large. Average length—8". Average width—1¼".
- *Form.*—Lanceolate. Acutely pointed.
- *Thickness.*—Medium.
- *Margin.*—Crenate.
- *Petiole.*—Short. Medium thickness.
- *Glands.*—Average number—2. Alternate. Small. Globose (same as Bonanza). Positioned on base of blade.
- *Color.*—Top Side—Medium green (23–L–8). Under Side—Lighter green (22–L–7).

Flowers:
- *Blooming Period.*—March 3rd–March 15th, 1973. Medium, as compared with other varieties.
- *Size.*—Large.

Fruit:
- *Maturity When Described.*—Eating ripe—July 25th, 1973.
- *Date of First Picking.*—July 14th, 1973.
- *Date of Last Picking.*—July 23rd, 1973.
- *Size.*—Uniform. Large. Average diameter axially—2½". Average transversely in suture plane—2½".
- *Form.*—*Uniform.* Symmetrical. Globose.
- *Suture.*—*Shallow.*—Extends from base to apex.
- *Ventral Surface.*—Rounded strongly.
- *Cavity.*—Elongated in suture plane. Average depth—½". Average breadth—¾".
- *Base.*—Rounded.
- *Apex.*—Short. Depressed.

Skin:
- *Thickness.*—Medium.
- *Texture.*—Medium.
- *Tendency To Crack.*—None noted.
- *Down.*—Scant. Short.
- *Color.*—Yellow (9–K–3 to 9–L–5) substantially overspread with red (6–L–7) shading darker to (7–L–7), with mottling on sunny side.

Flesh:
- *Juice.*—Moderate.
- *Texture.*—Firm. Crisp. Melting.
- *Ripens.*—Evenly.
- *Flavor.*—Subacid. Mild.
- *Aroma.*—Distinct.
- *Eating Quality.*—Fair to good.
- *Color.*—Yellow (10–L–5) flecked with red. Surface of pit cavity: Red (5–L–7).

Stone:
- *Type.*—Free.
- *Size.* — Small. Average length — 1⅛. Average breadth—1". Average thickness—⅝".
- *Form.*—Obovoid.
- *Base.*—Straight.
- *Apex.*—Rounded.
- *Sides.*—Equal.
- *Dorsal Edge.*—Full, with broad groove.
- *Color.*—Brown (56–L–3) with purplish cast.

Use: Market—local. Dessert.
Keeping quality: Medium.
Resistance to insects and diseases: No unusual susceptibilities noted.
Shipping quality: Medium.

The dwarf peach tree and its fruit herein described may vary in slight detail due to climatic and soil conditions under which the variety may be grown; the present description being of the variety as grown in the Central Valley of California.

I claim:

1. A new and distinct variety of genetically dwarf peach tree, substantially as illustrated and described, which is of medium size, medium vigorous, spreading, foliated with large lanceolate leaves having a crenate margin and globose glands, and a productive bearer of uniform, large, symmetrical, globose, freestone fruit having yellow skin substantially overspread with red, and firm, crisp, melting, yellow flesh flecked with red; the fruit of the variety being larger in size, firmer of flesh, and ripening at least one week earlier than the seed parent, Empress; and ripening about two weeks later than the pollen parent, Bonanza.

No references cited.

ROBERT E. BAGWILL, Primary Examiner